(12) United States Patent
Erdmann et al.

(10) Patent No.: US 7,247,448 B2
(45) Date of Patent: Jul. 24, 2007

(54) METHOD FOR GENE EXPRESSION

(75) Inventors: Volker A. Erdmann, Berlin (DE);
Thorsten Lamla, Berlin (DE);
Wolfgang Stiege, Berlin (DE)

(73) Assignee: RiNA Netzwerk RNA-Technologien GmbH, Berlin (DE)

( * ) Notice: Subject to any disclaimer, the term of this patent is extended or adjusted under 35 U.S.C. 154(b) by 75 days.

(21) Appl. No.: 10/486,416

(22) PCT Filed: Jul. 17, 2002

(86) PCT No.: PCT/DE02/02672

§ 371 (c)(1),
(2), (4) Date: Oct. 28, 2004

(87) PCT Pub. No.: WO03/016526

PCT Pub. Date: Feb. 27, 2003

(65) Prior Publication Data

US 2005/0227312 A1    Oct. 13, 2005

(30) Foreign Application Priority Data

Aug. 6, 2001   (DE) ................................ 101 37 792

(51) Int. Cl.
*C12P 21/00* (2006.01)
(52) U.S. Cl. ..................... 435/69.1; 536/23.1
(58) Field of Classification Search ...................... None
See application file for complete search history.

(56) References Cited

U.S. PATENT DOCUMENTS

| 4,452,682 | A  | * | 6/1984 | Takata et al. .......... 204/403.12 |
| 5,593,856 | A  |   | 1/1997 | Choi et al. ................. 435/68.1 |
| 6,168,931 | B1 | * | 1/2001 | Swartz et al. ............. 435/68.1 |
| 2002/0123101 | A1 | * | 9/2002 | Inoue et al. ............... 435/69.1 |

FOREIGN PATENT DOCUMENTS

| DE | 10137792 A1 | 2/2003 |
| EP | 0312617 B1 | 4/1989 |
| EP | 0314415 A2 | 5/1989 |
| EP | 0401369 B1 | 12/1990 |
| EP | 0593757 A1 | 4/1994 |
| EP | 1176210 A1 | 1/2002 |
| JP | 06262171 A * | 9/1994 |
| WO | WO9950436 * | 10/1999 |
| WO | WO0058493 * | 10/2000 |
| WO | WO 03/016526 A1 | 2/2003 |

OTHER PUBLICATIONS

Lamla et al., The Cell-Free Protein Biosynthesis-Applications and Analysis of the System, Acta Biochimica Polonica, 2001, vol. 48, No. 2, pp. 453-465.*

Zhou et al., Expression, Purification and Characterization of Beta Domain and Beta Domain Dimer of Metallothionein, Biochimica et Biophysica Acta, 2000, vol. 1524, pp. 87-93.*

Merk, Helmut; Stiege, Wolfgang; Tsumoto, Kouhei; Kumagai, Izumi; Erdmann, Volker A. "Cell-Free expression of two single-chain monoclonal antibodies against lysozyme: effect of domain arrangement on the expression". J. Biochem. vol. 125. 1999. pp. 328-333.

Zubay, Geoffrey. "In vitro synthesis of protein in microbial systems". Annual Reviews. 1973. pp. 267-287.

He, Mingyue; Taussig, Michael J. "Single step generation of protein arrays from DNA by cell-free expression and in situ immobilization (PISA method)". Nucleic Acids Research. vol. 29. No. 15 e73. 2001. pp. 1-6.

Lamla, Thorsten; Stiege, Wolfgang; Erdmann, Volker A. "An Improved Protein Bioreator". Molecular & Cellular Proteomics 1.6 2002. pp. 466-471.

* cited by examiner

*Primary Examiner*—Robert A. Wax
(74) *Attorney, Agent, or Firm*—Mayer & Williams PC; Keum J. Park, Esq.; Stuart H. Mayer, Esq.

(57) ABSTRACT

The invention relates to a method for gene expression in a cell-free transcription/translation system, the reaction solution containing all the components necessary for the transcription/translation mechanism, amino acids, nucleotides, metabolic components which provide energy and which are necessary for synthesis, and the proteins arising during translation being immobilized on a matrix.

26 Claims, 2 Drawing Sheets

SEQUENCE LISTING

<160> NUMBER OF SEQ ID NOS: 2

<210> SEQ ID NO 1
<211> LENGTH: 9
<212> TYPE: PRT
<213> ORGANISM: Artificial
<220> FEATURE:
<223> OTHER INFORMATION: Streptavidin binding sequence

<400> SEQUENCE: 1

Ala Trp Arg His Pro Gln Phe Gly Gly
1               5

<210> SEQ ID NO 2
<211> LENGTH: 8
<212> TYPE: PRT
<213> ORGANISM: Artificial
<220> FEATURE:
<223> OTHER INFORMATION: Streptavidin binding sequence

<400> SEQUENCE: 2

Trp Ser His Pro Gln Phe Glu Lys
1               5

US 7,247,448 B2

METHOD FOR GENE EXPRESSION

STATEMENT OF RELATED APPLICATIONS

Figure 1:
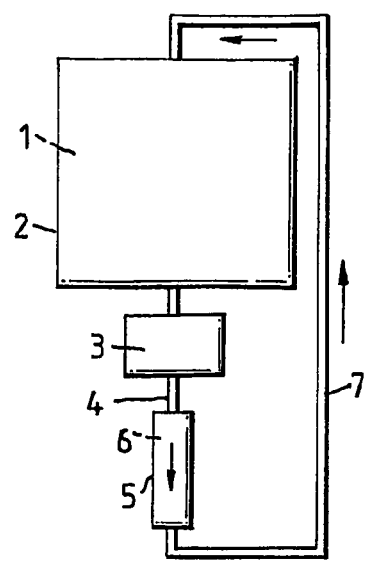

This application is a filing under 35 U.S.C. 371 of PCT International Patent Application No. PCT/DE02/02672, filed Jul. 17, 2002, which claims the benefit of priority of German Patent Application No. 101 37 792.4, filed Aug. 6, 2001.

FIELD OF THE INVENTION

The invention relates to a method for gene expression in a cell-free transcription/translation system, the reaction solution containing all the components necessary for the transcription/translation mechanism, amino acids, nucleotides, metabolic components which provide energy and which are necessary for synthesis. The proteins formed during translation are immobilized on a matrix.

Further, the invention relates to a device for cell-free gene expression in a transcriptionltranslation system.

PRIOR ART

Methods for the cell-free gene expression of proteins are known in the art, for instance, from the European Patent documents EP 0312 617 B1, EP 0401 369 B1 and EP 0 593 757 B1.

According thereto, the components, which are necessary for a transcription and/or translation, are incubated, in addition to a nucleic acid strand coding for a desired protein, in reaction vessel, and after the expression, the polypeptides/proteins are isolated from the reaction solution.

The components, which are necessary for transcription as well as for translation, can easily be obtained from the supernatants of prokaryotic or eukaryotic cell lysates after a centrifugation at e.g. 30,000 g. This so-called S30 extract contains all components, which are necessary for transcription and translation.

In most cases, the gene or the nucleic acid strand coding for the protein or peptide is under the control of a T7 promoter. This has the advantage that by the application of rifampicin, existing *E.coli* RNA polymerase can be inhibited, and thus any endogenous *E.coli* DNA originating from the S30 extract or from the vector preparation will not be transcribed. If, however, a gene under the control of an *E.coli* promoter is expressed, an *E.coli* polymerase must be used, which may lead to a co-expression of any endogenous *E.coli* DNA and thus to undesired endogenous proteins. Typically, the expression takes place at 37° C.; may however also take place from 17° C. to 45° C. The adjustment of the temperature is particularly recommended for the expression of proteins, wherein a complex secondary/tertiary structure is to be formed. By lowering the temperature, the synthesis rate can be reduced, increasing the likelihood of correctly folding the proteins, in order to obtain a functioning/active protein. In addition, influence can be exerted on the generation of disulfide bridges within the expressed proteins, via the reduction potential of the reaction solution by the addition of dithiothreitol (DTT) and/or oxidized/reduced glutathione.

Prior to every new protein synthesis, the respective systems have to be subjected to an optimization. Thereby, the concentrations of the bivalent magnesium ions ($Mg^{2+}$), of the RNA/DNA polymerase and of the coding nucleic acid strand serving as a matrix are varied.

In the method for the cell-free expression of proteins disclosed in the document EP 0312 617 B1, the nucleic acid strand coding for the protein is added as mRNA to the reaction solution. Therewith, for the production of polypeptides in the cell free-system, only the components of the translation apparatus necessary for translation, in particular ribosomes, initiation, elongation, release factors and aminoacyl tRNA synthetase, as well as amino acids and ATP and GTP as substances, which provide energy, are fed to a reaction vessel. In the subsequent polypeptide/protein synthesis, there will also be generated, beside polypeptides/proteins, low-molecular substances, such as ADP, AMP, GDP, GMP and inorganic phosphates under consumption of the substances ATP and GTP, which provide energy, and of amino acids. This leads to the reaction coming to an end after approx. 30 to 60 minutes after consumption of ATP or GTP or of an amino acid or by the generated low-molecular substances acting as inhibitors. In order to act against this, the document EP 0312 617 B1 discloses that the substances consumed during translation are removed during translation, and simultaneously, substances, that provide energy and amino acids are added in order to maintain the initial concentration.

On the other hand, the document EP 0401 369 B1 discloses a method, wherein the nucleic acid strand coding for the protein can be added as mRNA or DNA to the reaction solution. The latter has the advantage that DNA is substantially more stable than mRNA, and the necessary transcription of the DNA into RNA prior to the reaction is not required, and the DNA can be used immediately, e.g. as a vector or a linear construct. By the use of the DNA, the cell-free expression system must contain, beside the above translation factors, also transcription factors necessary for transcription of the DNA into RNA, such as RNA polymerase, RNA factor and rho protein and the nucleotides ATP, UTP, GTP and CTP. Here, too, the low-molecular substances consumed during transcription/translation, such as ADP, AMP, GDP, GMP and inorganic phosphates, have to be removed during translation, and simultaneously the substances, which provide energy, nucleotides and the amino acids have to be added for maintaining the initial concentration.

Both prior art methods have the disadvantage that the translated proteins remain dissolved in the reaction vessel during the complete reaction time, and can only be removed from the reaction solution after the reaction by suitable purification methods. This leads to the result that after protein expression, a time-consuming separate method step must follow, during which it must be permitted that the proteins bind to a matrix or the like, in order to separate it from the remaining components of the reaction solution.

Another problem is that during the expression, which may take up to 100 hours, no information about the amount and/or activity of generated protein can be obtained without sampling. By the sampling, however, part of the solution would be removed from the reaction system, which will lead to a lower total yield. The control of protein synthesis is necessary since lack of any one of the many components necessary for transcription/translation causes the synthesis rate to be dramatically reduced or even completely stopped. Further, the expressed proteins may be precipitated at higher concentrations or inhibit their own synthesis as a product.

From the document EP 0 593 757 B1 it is taught in the art to also separate, in addition to the consumed low-molecular substances, the expressed polypeptides from the reaction solution by an ultrafiltration barrier during translation. This separation of the polypeptides then takes place exclusively via the pore size of the used ultrafiltration barrier/membrane and has the disadvantage that there is a strict limit in the choice of the pore size, since the pore size must not be so large that the factors and enzymes necessary for transcription/translation can pass through the membrane. Thus, only smaller polypeptides can be separated, not however bigger polypeptides or even proteins. Further, interactions may occur between proteins and the ultrafiltration barrier/membrane, which may reduce the yield of proteins.

TECHNICAL OBJECT OF THE INVENTION

It is the object of the invention to develop a method for gene expression in a cell-free transcription/translation system, wherein a separation of product/protein may take place easily and without a separate isolation step, and wherein the amount of expressed polypeptide/protein can be determined prior to the end of the reaction. In particular, it is intended that the proteins obtained during the reaction should be separable from the reaction solution irrespective of their size.

BASICS OF THE INVENTION AND PREFERRED EMBODIMENTS

For achieving the above technical object, the invention teaches that the generated proteins are immobilized during transcription/translation on a matrix. In other words, it is not two methods steps, transcription/translation and subsequent product separation, which are used, but the immobilization is performed at the beginning of transcription/translation already and is maintained during transcription/translation, i.e. takes place in parallel to the gene expression. At the end of the reaction, the immobilization product is taken out, and the immobilized protein is separated again.

By means of the invention, a substantial simplification of the method steps is achieved. Further, the product/protein is continuously removed, so that it cannot disturb transcription/translation. Thereby, such proteins will also be accessible for synthesis, which would otherwise provide very small yields only, if at all, due to negative interactions with the system.

This immobilization may take place inside as well as outside the reaction vessel; the latter has an independent significance. If the proteins are bound inside the reaction vessel, the matrix binding the protein is added to the reaction mixture prior to the reaction and remains in the reaction vessel during the incubation time. After the incubation, the matrix with the protein bound thereto is isolated from the reaction solution. This may take place, for example, by filtration or centrifugation. Thus the time-consuming binding of the proteins to the matrix after the incubation for isolating/cleaning them is not required, in contrast to the prior art.

By a protein determination before and behind the separate reaction vessel (e.g. a column), the absorbed protein amount can be determined by the difference in the protein amounts. When the matrix specifically binds to the expressed protein, the amount of expressed protein may be measured, and, within the lapsed period of time, the expression/synthesis rate can also be determined. In the simplest case, the determination of the protein concentration is made by a measurement of the absorption of the reaction solution at the wavelength 1 to 280 nm. By using the extinction coefficient, the protein amount in the solution can be determined according to the Lambert-Beer law. In order to determine the protein concentration as precisely as possible, it is in fact reasonable to also determine, in addition to the protein concentration, the nucleotide concentration in the reaction solution. This may, for instance, be performed by measuring the absorption at 2 to 260 nm, which makes it possible to determine the contents of nucleotides in the solution. Thereby, mistakes in the protein determination, in particular by measuring the absorption, can be avoided, since high nucleotide concentrations may affect the protein measurement.

Further it is possible, during the incubation time already, not only to bind the protein, but also to isolate the bound protein from the matrix. For this purpose, the matrix, which is in a separate reaction vessel/column, is decoupled from the cycle, and the cycle may then, for instance, redirected to a parallel matrix. Compared to the separation described in the document EP 593757 B1, the invention has the advantage that the proteins immobilized at the matrix are already concentrated, and thus only a small part of the reaction solution needs to be removed from the system. Further, the separation is different from the method disclosed in the document EP 593757 B1, independent from the size of the proteins, since they are separated from the reaction solution according to their size, but are specifically immobilized at a matrix. Thus, such proteins can also be removed from the reaction solution, which are for instance as big as the proteins in the solution necessary for transcription/translation. It is therefore possible to separate the low-molecular metabolic products having a size less than 10 kD by a membrane, and to simultaneously keep the proteins, which are necessary for transcription/translation and which are typically larger than 50 kD, in the solution, and to simultaneously bind the expressed proteins to the matrix irrespective of their size.

It is further helpful in this context to determine the protein concentration before and behind the column according to the method described above, in order to obtain the optimum feeding to the column, and to thus minimize the loss of reaction solution. An optimum feeding of the matrix is achieved, if the protein concentrations before and behind the column are identical, and thus no protein will further bind to the column.

The extraction of the proteins prior to the end of the reaction already is particularly recommended, if the proteins have a significant activity, such as the kinases. Herein, an observation of missing activity is a termination criterion for the method, after a period of time already, which is a small fraction of the total duration of the reaction, for instance ¹/₁₀ or ¹/₂₀ or less. Also, by extraction, the quality, of the proteins can already be determined during the process, without significant losses of reaction solution.

Finally, it can be prevented, by the immobilization, that the expressed proteins will be precipitated at higher concentrations or inhibit their own synthesis as a product.

The functioning of the matrix can be based on all cleaning methods known for the binding of proteins, such as ion exchangers, affinity, antigen/antibody interaction, hydrophobic/hydrophilic interaction.

For a particularly efficient purification of the proteins, they can be co-expressed as a so-called fusion protein with one or several markers, e.g. in the form of N or C terminal successive histidines, or one or several other proteins, e.g. glutathione. The matrix has in this case for this marker/protein a specific binding partner permitting an efficient binding of the chimeric fusion protein via the marker/fusion partner to the matrix.

In order to guarantee a continuous protein expression, the substances consumed during transcription/translation can be extracted during transcription/translation, and simultaneously, the substances, which provide energy, and the amino acids for maintaining the initial concentration can be introduced via a semi-permeable membrane. Furthermore, the consumed low-molecular substances can be separated from the reaction solution by an ultrafiltration membrane during transcription/translation, whereas simultaneously, the substances, which provide energy, can be added via a pump, and the amino acids for maintaining the initial concentration can be added via another pump.

In principle the invention can be used in prokaryotic systems as well as in eukaryotic systems.

With regard to the method, it is preferred that the matrix is outside the reaction vessel, preferably in another reaction vessel, most preferably in a column. Further it is preferred that the protein concentration is determined before and behind the matrix, preferably by absorption of light, in particular in the u.v. range. The matrix can specifically bind proteins because of the hydrophobic and/or hydrophilic or antigen/antibody or ionic interactions. Herein, the suitable molecules are bound to the surface of a substrate.

The matrix may contain anion or cation exchange material or hydroxyapatide. If the proteins are expressed as fusion proteins, and the fusion partners are at the N, C terminal or within the expressed protein, a matrix can be used, which specifically binds the fusion partner. For instance, the protein may contain at the N or C terminal, several successive histidines, in particular 3 to 12, preferably 5 to 9, most preferably 6, and the matrix may then carry a metal chelate compound, in particular with bivalent metal ions, preferably bivalent copper and/or nickel ions. The protein may contain at the N or C terminal, glutathione S-transferase as a fusion partner, and glutathione may be coupled to the matrix. The protein may contain an amino acid sequence permitting it to bind to streptavidin, preferably the amino acid sequence A WRHPQFGG, most preferably the amino acid sequence WSHPQFEK, and then streptavidin may be coupled to the matrix.

Generated low-molecular metabolic products can be extracted during the expression, and consumed necessary metabolic components of the reaction can be added in an amount that the initial concentrations of the low-molecular metabolic products and the necessary metabolic components remain constant, said necessary metabolic components being formed from the not closed group "ATP, UTP, GTP and CTP, pyrophosphate and amino acids", and said low-molecular metabolic products being formed from the not closed group "ADP, AMP, GDP, GMP and inorganic phosphate". Via a semi-permeable membrane, the necessary metabolic components can be added and the low-molecular metabolic products can be extracted.

In the following, the invention is explained in more detail, with reference to drawings representing just embodiments and to an example. There are:

FIG. 1 a diagrammatical representation of a device according to the invention comprising a reaction vessel, a column containing the matrix, and a pump.

Figure 2:
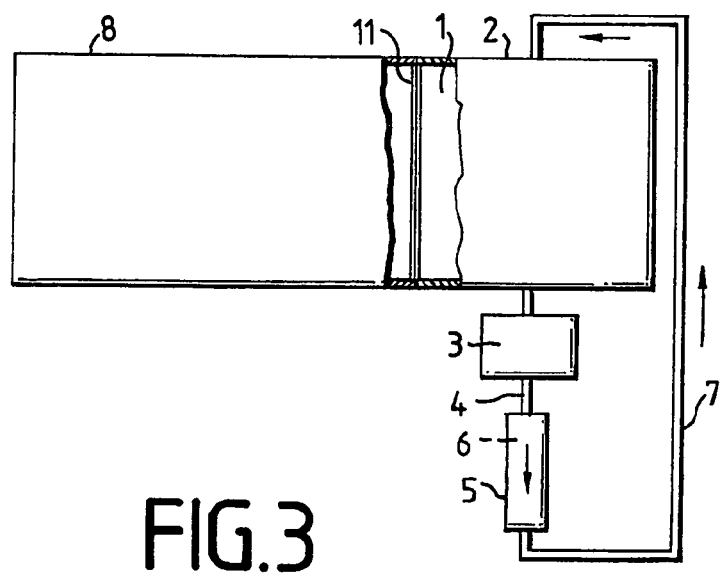

FIG. 2 a diagrammatical representation of a device according to the invention comprising a reaction vessel, a colunm containing the matrix, and a pump, wherein the necessary metabolic components are added via a semi-permeable membrane, and the low-molecular metabolic products are extracted (semi-continuous cell-free reactor).

Figure 3:
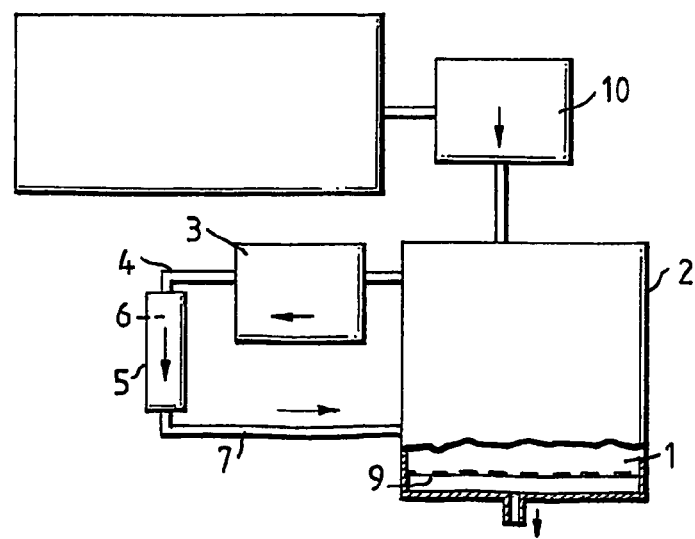

FIG. 3 a diagrammatical representation of a device according to the invention comprising a reaction vessel, a column containing the matrix, and a pump, wherein low-molecular metabolic products are extracted via an ultrafiltration membrane (continuous cell-free reactor).

Figure 4:
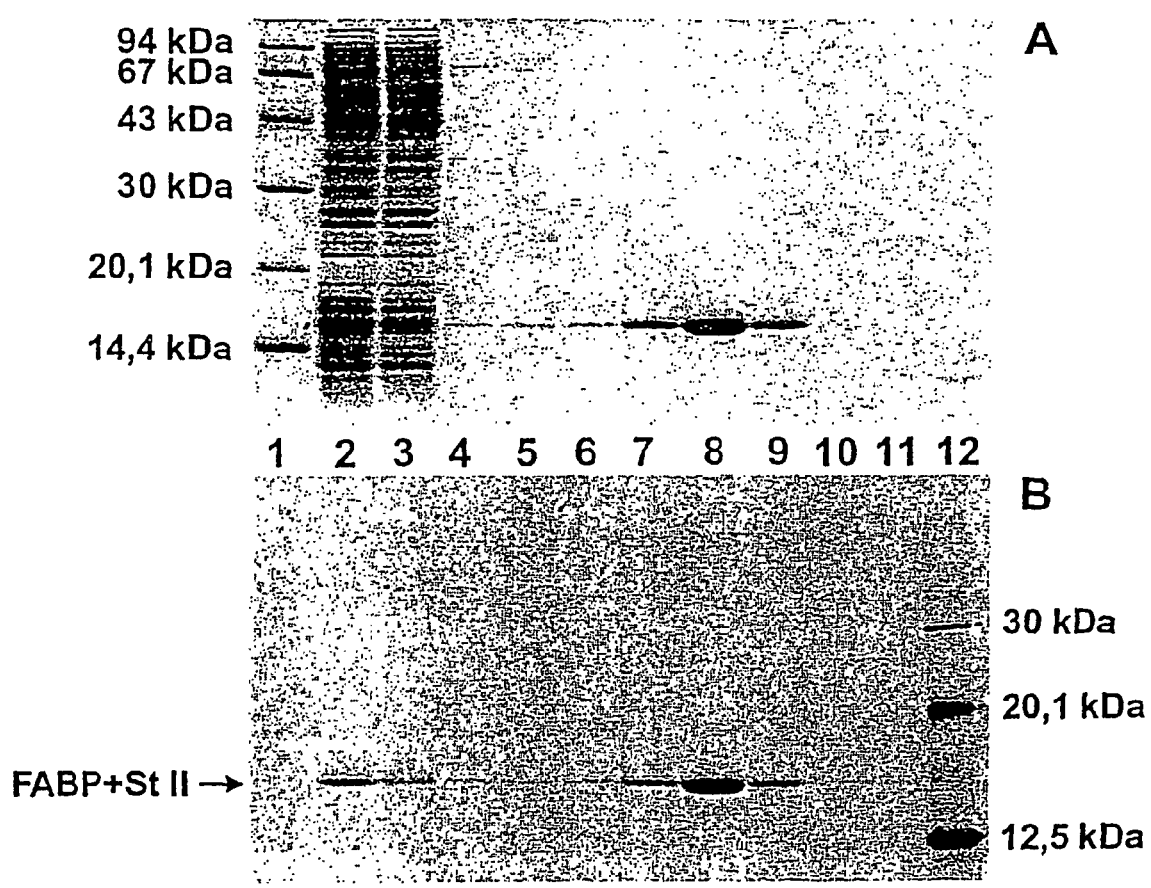

FIG. 4 the isolation of the FABP with Strep-tag II from the semi-continuous cell-free reactor during the synthesis with a StrepTactin® (Institute für Bioanalytik Göttingen, Germany) Sepharose column. There were applied 15 μl of every isolated fraction and analyzed with SDS-PAGE under reducing conditions. The samples were applied as follows: (1) molecular weight marker; (2) reaction solution; (3 to 5) wash fractions 1 to 3; (6 to 11) eluted fractions 1 to 6, and (12) L[14C]-leucin molecular weight marker. (A) Coomassie stained SDS-PAGE and (B) autoradiogram of the SDS-PAGE.

In FIG. 1 can be seen a reaction chamber 2 receiving the reaction solution 1, with transcription/translation taking place in said reaction chamber 2. A pump 3 pumps the reaction solution 1 through an inlet 4 on the matrix 6 being accommodated in a separate reaction vessel, namely a column 5, and through an outlet 7 back into the reaction vessel 2.

FIG. 2 shows a device according to the invention being complemented compared to the subject matter of FIG. 1, wherein a semi-permeable membrane connects the reaction chamber 2 to a storage vessel 8. Through the semi-permeable membrane 11, the substances consumed during transcription/translation are extracted during transcription/translation, and simultaneously the substances, which provide energy, and the amino acids for maintaining the initial concentrations, are supplied.

FIG. 3 shows a device according to the invention with additional features compared to the subject matter of FIG. 1, wherein the consumed low-molecular substances be separated from the reaction solution 1 by an ultrafiltration membrane 9 during transcription/translation, whereas simultaneously, by another pump 10, the substances which provide energy and the amino acids for maintaining the initial concentration can be supplied from a storage vessel 8.

EXAMPLE

A coupled transcription/translation was performed in a semi-continuous cell-free reactor according to FIG. 2 for 20 hours at 30° C. The reaction chamber 2 had a volume of 750 μl, and in connection with volumes of the pump 3, the inlet 4, outlet 7, and of the column, a total volume of the reaction solution 1 of 2,150 μl resulted. The reaction solution for the coupled transcription/translation system is based on an *E.coli* S30 lysate (strain D10). The used plasmid was pHMFH+StII. The starting vector for this plasmid was pUC18. Herein, the SphI/EcoRI fragment from pET3d (Novagen) was cloned. Into this modified vector, the FABP gene (fatty acid binding protein) was cloned over NcoI/BamHI. The used transcription/translation system has been described by Zubay, G. (Annu. Rev. Genet. 7, 267-287), and was completed with 500 U/ml T7 phage RNA polymerase (Stratagene, La Jolla, Calif.) and 200 μM L[14C]-leucin (25 dpm/pmol, obtainable from 150 μM "cold" and 50 μM "hot" leucin, Amersham (Biosciences, Piscataway, N.J.), 100 dpm/pmol). The nucleic acid strand coding for FABP was added to the system in the form of the above plasmid in a concentration of 2 nM, wherein the FABP is expressed with a C-terminal Strep-tag II.

Into the storage vessel were brought 6 ml translation buffer (50 mM HEPES-KOH, (pH 7.6), 70 mM KOAc, 30 mM NH4Cl, 10 mM MgCl2, 0.1 mM EDTA (pH 8.0), 0.002% NaN3) with 5 mM dithiothritole, 4 mM MgCl2, 0.02% NaN3; 100 μM folic acid, 400 μM L[14C]-leucin (0.75 dpm/pmol, obtainable from 397 μM cold and 3 μM hot leucin; Amersham, 100 dpm/pmol), 400 μM of each of the other 19 amino acids, 1 mM each of ATP and GTP, 0.5 mM each of CTP and UTP, 30 mM phosphoenolpyruvate (Boebringer Mannheim), 10 nM acetyl phosphate (Sigma). During the synthesis, the reaction solution 1 was continuously pumped with a flow rate of approx. 0.07 ml/min by means of the pump 3 from the reaction vessel 2 through the inlet 4 on the matrix 6 in the column 5, and through the outlet 7 back again into the reaction vessel 2. As the matrix, 530 µl StrepTactin® Sepharose (IBA Goettingen) were used.

For isolating the bound product, the StrepTactin® Sepharose was eluted three times with 800 µl washing buffer (100 mM Tris-HCl (pH 8.0), 150 mM NaCl, 1 mM EDTA), and the fusion product was eluted six times with elution buffer (50 mM HEPES-KOH (pH 7.6), 70 mM KOAc, 30 mM NH4Cl, 10 mM MgCl2, 0.1 mM EDTA (pH 8.0), 0.002% NaN3, 2.5 mM desthiobiotin).

The measurement of the incorporation of the L[14C]-leucin in the synthesized protein was performed by scintillation counting of material precipitated with trichloroacetic acid, as described by Merk, H., Stiege, W., Tsumoto, K., Kumagai, I. and Erdmann, V. A. (1999, J. Biochem. 125, 328-333). It could be shown that 41% of the expressed protein remained in the reaction solution, 13% were in the fraction eluted with the washing buffer, and 46% of the expressed protein could be eluted by the column. The expressed proteins were further dissociated in the polyacrylamide gel electrophoresis (SDS-PAGE) under denaturated conditions and analyzed by Coomassie staining and by means of the PhosphorImager system (Molecular Dynamics). The above distribution of the expressed proteins over the individual fractions could be confirmed in the Coomassie (FIG. 4A) stained SDS-PAGE as well as in the corresponding autoradiogram (FIG. 4B). By extension of the matrix, a clear displacement of the protein bound to the matrix could be achieved.

vessel containing all components necessary for transcription/translation mechanism, amino acids, nucleotides, metabolic components which provide energy and which are necessary for the synthesis, wherein proteins arising during transcription/translation are immobilized on a matrix such that the reaction solution is conducted over the matrix disposed outside the reaction vessel and in a separate immobilization vessel passed by the reaction solution, wherein the concentration of the proteins is determined before and behind the matrix with respect to the direction of flow of the reaction solution through the matrix.

2. A method according to claim 1, wherein the concentration of proteins arising during transcription/translation is determined before and behind the matrix by measuring the absorption of light.

3. A method according to claim 1, wherein the matrix specifically binds proteins by hydrophobic, hydrophilic, antigen/antibody, or ionic interactions.

4. A method according to claim 1, wherein the matrix contains anion or cation exchange material or hydroxyapatide.

5. A method according to claim 1, wherein the proteins are expressed as fusion proteins containing a fusion partner.

6. A method according to claim 5, wherein the fusion partners are located at the N terminal, C terminal or within the expressed protein.

7. A method according to claim 5 wherein a matrix is used which specifically binds to the fusion partner.

8. A method according to claim 6, wherein the protein contains at the N terminal or C terminal one or more successive histidines.

9. A method according to claim 1, wherein the matrix carries a metal chelate compound comprising bivalent metal ions.

The invention claimed is:

1. A method for gene expression in a cell-free transcription/translation system, the reaction solution in a reaction 10. A method according to claim 6, wherein the protein contains at the N terminal or C terminal glutathione S-transferase as a fusion partner.

11. A method according to claim 10, wherein glutathione is coupled to the matrix.

12. A method according to claim 5, wherein the protein contains an amino acid sequence permitting it to bind to streptavidin.

13. A method according to claim 12, wherein streptavidin is coupled to the matrix.

14. A method according to claim 1, wherein generated low-molecular metabolic products are extracted during the expression, and consumed necessary metabolic components of the reaction are added in an amount such that the concentrations of the low-molecular metabolic products and the necessary metabolic components during the duration of the reaction differ by less than 80% of their respective initial concentrations.

15. A method according to claim 1, wherein the necessary metabolic components contain a substance of the group comprising "ATP, UTP, GTP and CTP, pyrophosphate, amino acids, and mixtures of these substances".

16. A method according to claim 14, wherein the necessary metabolic components are added via a semi-permeable membrane, and the low-molecular metabolic products are extracted via a semi-permeable membrane comprising the same or different semi-permeable membrane.

17. The method of claim 1, wherein the separate reaction vessel comprises a column.

18. The method of claim 2, wherein the absorption is measured of light in the u.v. range.

19. The method of claim 8, wherein the histidines comprise 3 to 12 successive histidines.

20. The method of claim 8, wherein the histidines comprise 5 to 9 successive histidines.

21. The method of claim 8, where the histidines comprise 6 successive histidines.

22. The method of claim 9, wherein the metal chelate compound comprises bivalent copper or nickel ions.

23. The method of claim 14, wherein the concentrations of the low-molecular metabolic products and the necessary metabolic components during the duration of the reaction differs by less than 50% of their respective initial concentrations.

24. The method of claim 14, wherein the concentrations of the low-molecular metabolic products and the necessary metabolic component during the duration of the reaction differs by less than 20% of their respective initial concentrations.

25. The method of claim 16, wherein the semi-permeable membrane has cut-off limits in the range of 500 to 20,000 Da.

26. The method of claim 16, wherein the semi-permeable membrane has cut-off limits in the range of 3,000 to 5,000 Da.

* * * * *